US 6,551,513 B2

(12) United States Patent
Nikaido et al.

(10) Patent No.: US 6,551,513 B2
(45) Date of Patent: Apr. 22, 2003

(54) CLEANING AND PRIMING METHOD FOR DIALYSIS SYSTEM

(75) Inventors: Taku Nikaido, Osaka (JP); Mitsutaka Ueda, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/886,986

(22) Filed: Jun. 25, 2001

(65) Prior Publication Data

US 2001/0035378 A1 Nov. 1, 2001

Related U.S. Application Data

(62) Division of application No. 09/413,817, filed on Oct. 7, 1999, now Pat. No. 6,277,272.

(30) Foreign Application Priority Data

Oct. 7, 1998 (JP) ............................................ 10-258711

(51) Int. Cl.[7] ......................... B01D 65/00; B01D 65/02; B01D 61/26
(52) U.S. Cl. ............. 210/646; 210/321.69; 210/321.71; 210/645; 210/791; 210/805
(58) Field of Search .................................. 210/645, 646, 210/805, 321.69, 791, 321.71

(56) References Cited

U.S. PATENT DOCUMENTS

| | | | | |
|---|---|---|---|---|
| 4,495,067 A | * | 1/1985 | Klein et al. | |
| 4,935,125 A | * | 6/1990 | Era et al. | |
| 5,259,961 A | * | 11/1993 | Eigendorf | 210/646 |
| 5,690,831 A | * | 11/1997 | Kenley et al. | |
| 5,863,421 A | * | 1/1999 | Peter, Jr. et al. | 210/646 |
| 6,132,616 A | * | 10/2000 | Twardowski et al. | 210/646 |

FOREIGN PATENT DOCUMENTS

| | | |
|---|---|---|
| EP | 0 826 383 A | 3/1998 |
| JP | 3254755 | 11/1991 |
| JP | 8080346 | 3/1996 |
| JP | 8150201 | 6/1996 |
| JP | 8-080346 | 7/1996 |
| WO | WO 00 06217 A | 2/2000 |

* cited by examiner

Primary Examiner—John Kim
(74) Attorney, Agent, or Firm—Kubovcik & Kubovcik

(57) ABSTRACT

A dialysis system which does not need to use a physiological saline in replenishing a solution or cleaning and priming the dialysis system, does not need a troublesome setting operation and can easily and accurately set a flow rate of a replenisher solution. The dialysis system includes a closed type water-removal control apparatus 1, a dialyzer 2, a fresh dialysate line 3 as well as a used dialysate line 4, a dialysate pressurizing line 5, a dialysate pressurizing pump 51 provided in the dialysate pressurizing line 5, an artery side blood line 6, a blood pump 61 provided in the artery side blood line 6 and a vein side blood line 7. According to the dialysis system, by pressurizing a dialysate into a communication line of the dialysate, the dialysate is made to flow from a dialysate flow path 21 into a blood flow path 22 through a dialysis membrane 23 of the dialyzer 2 and the inside of a blood circulation path can be cleaned and primed.

2 Claims, 8 Drawing Sheets

Artery side Vein side

CLEANING AND PRIMING METHOD FOR DIALYSIS SYSTEM

This application is a division of application Ser. No. 09/413,817, filed Oct. 7, 1999, U.S. Pat. No. 6,277,272.

BACKGROUND OF THE INVENTION

1. Field of the Invention

The present invention relates to a dialysis system and a method of cleaning and priming a blood circulation path of the dialysis system. More particularly, the invention relates to a dialysis system capable of using a dialysate in place of physiological saline as a replenisher solution when blood pressure is lowered and capable of using a dialysate in place of physiological saline in a cleaning and priming operation and in a blood returning operation in blood dialysis treatment, and relates to a method of cleaning and priming of the dialysis system.

2. Description of the Prior Art

A dialysate is used in blood dialysis. Air or filled sterilized water is contained in a dialyzer before the dialyzer is used in blood dialysis and the air or the sterilized water needs to be removed. Therefore, as a pretreatment, conventionally, the inside of a dialyzer and the inside of a blood line connected to the dialyzer (hereinafter, referred to as the inside of a blood circulation path) are cleaned and primed by using, for example, physiological saline (normally, about 500 through 1000 ml).

Further, after finishing blood dialysis, blood remaining in the inside of the blood circulation path needs to be returned into the body of a patient who has undergone the blood dialysis treatment (referred to as blood returning) as much as possible, and as a post treatment, conventionally, blood is returned into the human body by using, for example, physiological saline (about 300 ml).

However, since physiological saline is expensive, a conventional blood dialysis system using a large amount thereof is problematic because of the considerable cost of the blood dialysis.

Hence, in order to resolve such a drawback, there have been proposed a method and an apparatus of blood dialysis (Japanese Unexamined Patent Publication No. 80346/1996) capable of achieving a reduction in the cost of the blood dialysis by reducing the volume of physiological saline used in the priming and blood returning operations, and a physical solution treating apparatus (Japanese Unexamined Patent Publication No. 150201/1996) capable of using a dialysate in place of physiological saline used in the priming and blood returning operations.

According to the blood dialysis system of Japanese Unexamined Patent Publication No. 80346/1996, when a blood dialysis operation is stopped, dialysate from a dialysate supply source is filtered to clean the dialysate and the provided filtered dialysate is pressurized from a dialysate flow path of a dialyzer to a blood flow path through dialysis membranes constituting a dialysis element. However, according to the method, in respect of blood remaining in a blood circulation path upstream from the blood flow path, the blood needs to be pushed out to the blood flow path by using physiological saline. Thus, despite the improvement, there is a drawback in that a necessary amount of physiological saline needs to be prepared and the operation takes time and labor.

Meanwhile, according to the physical solution treating apparatus of Japanese Unexamined Patent Publication No. 150201/1996, a dialysate reservoir bag is connected to an intermediate point of an artery side line through a branch tube and dialysate in the dialysate reservoir bag can be transferred to prime a blood chamber and a vein side line through the artery side line. However, according to the method, there are drawbacks in that not only is the dialysate reservoir bag expensive but also an operation of filling the dialysate into the bag becomes necessary and the operation is troublesome.

Further, there is a case in which a replenisher solution (normally, physiological saline is used) is injected into the body of a patient when the blood pressure of the patient is lowered during blood dialysis treatment, and in infusing the replenisher solution, conventionally, there are adopted methods, for example, as illustrated in FIG. 7 and FIG. 8.

According to the method illustrated in FIG. 7, a replenisher solution supply source 105 is connected to a blood circulation path 101 and the replenisher solution is infused while stopping the blood dialysis operation. As the replenisher solution supply source 105, a bottle or a bag filled with sterilized replenisher solution is generally adopted. In replenishing the solution, a valve 106 is closed, a valve 107 is opened and the replenisher solution is infused from the replenisher solution supply source 105 into the blood circulation path 101 by a blood pump 104. Flow rate of the replenisher solution is determined by the blood pump 104. Further, in the drawing, numeral 100 designates a dialyzer and numerals 102 and 103 designate drip chambers.

According to the method illustrated in FIG. 8, a replenisher solution line 209 is separately provided and a dialysate in a dialysate circulation path 206 which is cleaned by endotoxin filters 207 and 208 is infused into a blood circulation path 201. The replenisher solution line 209 is provided with an endotoxin filter 211 for further cleaning the dialysate and the replenisher solution is infused by a replenisher solution pump 210. Further, in the drawing, numeral 200 designates a dialyzer and numeral 205 designates a closed type water-removal control apparatus.

However, according to the method illustrated in FIG. 7, the replenisher solution needs to be prepared, the setup operation of connecting the replenisher solution supply source to the blood line and adding the replenisher solution (the case of a large amount of the replenisher solution) requires additional labor, and there are drawbacks in that there is a danger of erroneous operation or contamination since the replenishing operation is comparatively troublesome and that the cost is considerable.

Meanwhile, according to the method illustrated in FIG. 8, the dialysate is infused directly into the blood circulation path and accordingly, two of the endotoxin filters are normally needed and the cost is increased. Further, although the solution needs to be replenished when the blood pressure is lowered, according to the system of FIG. 8, water is removed by the dialyzer by a volume of the replenished solution and accordingly, there is a drawback in that the solution cannot be substantially replenished.

SUMMARY OF THE INVENTION

The invention has been carried out in view of the above-described situation and it is an object thereof to provide a dialysis system which does not need to use physiological saline in replenishing a solution or in cleaning and priming the dialysis system, does not need a troublesome setup operation and replenishing of the solution can easily and accurately be set with the flow rate of a replenisher solution.

As a result of intensive study in view of the above-described situation, the inventors have conceived of a system in which a pump for infusing a dialysate is provided in a communication line of the dialysate and the dialysate is pressurized into a closed communication line of the dialysate and by which the dialysate is infused from a side of a dialysate chamber to a side of a blood chamber of a dialyzer, and completed the invention. That is, according to an aspect of the invention, there is provided a method of cleaning and priming a dialysis system which includes a closed-type water-removal control apparatus, a dialysate line, a dialyzer and a blood line wherein a dialysate is made to flow into a blood circulation path through a membrane of the dialyzer by pressurizing the dialysate from a dialysate source into a closed communication line of the dialysate. In this case, it is preferable that the dialysis system is a dialysis system for central dialysate(i.e., multiple persons) supply.

Further, according to another aspect of the invention, there is provided a dialysis system comprising a dialyzer having a dialysate flow path and a blood flow path partitioned by a dialysis membrane, a closed-type water-removal control apparatus for controlling a difference between volumes of fresh dialysate flowing into the dialyzer and used dialysate flowing out of the dialyzer by removing a volume of water, a dialysate line connecting the closed-type water-removal control apparatus and the dialysate flow path of the dialyzer, a dialysate pressurizing line branched between a dialysate source and the closed-type water-removal control apparatus and connected to a communication line of the dialysate, a dialysate pressurizing pump provided in the dialysate pressurizing line, an artery side blood line connected to a blood inlet of the dialyzer, a blood pump provided in the artery side blood line and a vein side blood line connected to a blood outlet of the dialyzer. In this case, it is preferable that the dialysis system is a dialysis system for central dialysate supply. Further, it is preferable that the dialysate pressurizing pump is controlled by pressure of the dialysate and/or pressure of the vein. The dialysate pressurizing pump can also be set with a flow rate and a volume of pressurizing dialysate. An endotoxin filter can be provided in the dialysate line between the dialysate pressurizing line and the dialyzer.

DETAILED DESCRIPTION OF THE PREFERRED EMBODIMENTS

An explanation will be given of embodiments of the invention with reference to the drawings as follows.

Figure 1:
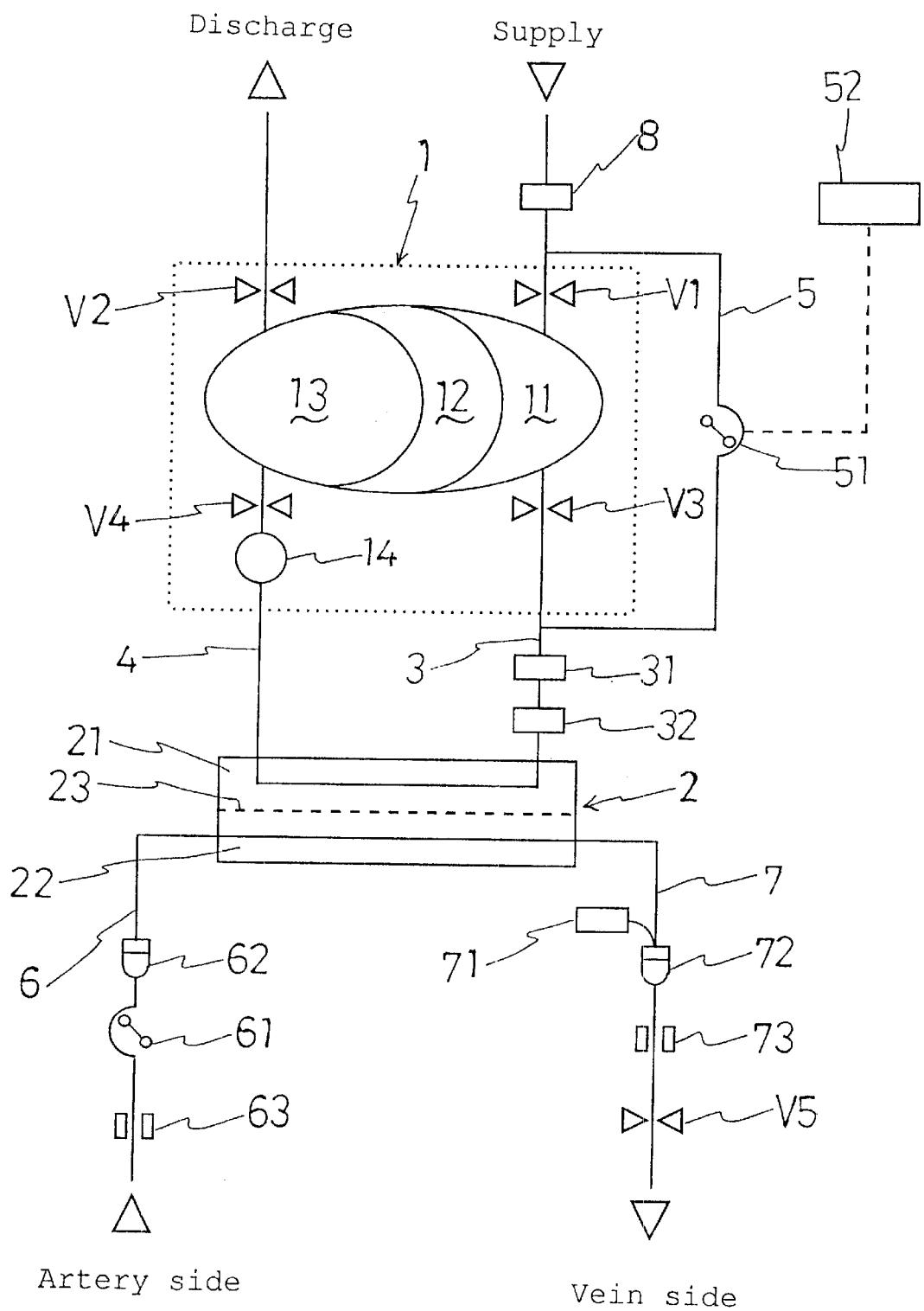
FIG. 1 is an outline constitution view of an embodiment of the invention.

As illustrated in FIG. 1, a dialysis system according to the invention includes a dialyzer 2, a closed-type water-removal control apparatus 1 for controlling a difference between volumes of a fresh dialysate flowing into the dialyzer 2 and a used dialysate flowing out of the dialyzer 2 according to a water-removal amount, a fresh dialysate line 3 as well as a used dialysate line 4, a dialysate pressurizing line 5, a dialysate pressurizing pump 51 installed in the dialysate pressurizing line 5, an artery side blood line 6, a blood pump 61 installed in the artery side blood line 6 and a vein side blood line 7. According to the dialysis system, the dialysate is pressurized from the dialysate pressurizing line 5 into a communication line of the dialysate which includes the closed-type water-removal control apparatus 1, the fresh dialysate line 3 and the used dialysate line 4, by means of which the dialysate is made to flow from a dialysate flow path 21 into a blood flow path 22 through a dialysis membrane 23 of the dialyzer 2 to thereby clean and prime an inside of a blood circulation path including the blood flow path 22 and the blood lines 6 and 7.

Further, according to FIG. 1, the dialysate pressurizing line 5 is connected to the fresh dialysate line 3 and the fresh dialysate line 3 is installed with an endotoxin filter 31 preferably downstream from a portion thereof connected with the dialysate pressurizing line 5. Further, in the drawing, numeral 8 designates an endotoxin filter, numeral 14 designates a solution pressurizing pump, numeral 32 designates a dialysate line pressure sensor, numeral 52 designates a control apparatus, numerals 62 and 72 designate drip chambers, numerals 63 and 73 designate air bubble sensors, numeral 71 designates a blood line pressure sensor and notations V1, V2, V3, V4 and V5 designate opening and closing valves.

As the closed-type water-removal control apparatus 1, there is adopted an apparatus disclosed in, for example, Japanese Patent Publication No. 82/1981 (U.S. Pat. No. 4,676,905), Japanese Unexamined Patent Publication No. 66761/1982 or Japanese Patent Publication No. 54590/1991 (U.S. Pat. No. 4,935,125), the disclosure of each of which is incorporated herein by reference. FIG. 1 illustrates an apparatus similar to that disclosed in Japanese Patent Publication No. 54590/1991. The apparatus is provided with a constant volume chamber partitioned into a fresh dialysate chamber 11 and a used dialysate chamber 13 by a flexible partition wall 12 filled with silicone oil, and when an opening and closing valve V1 is opened, dialysate from a dialysate source (not illustrated) is filled in the fresh dialysate chamber 11. Further, the dialyzer 2 is provided with the dialysate flow path 21 and the blood flow path 22 partitioned by the dialysis membrane 23 and an inlet and an outlet of the dialysate flow path 21 of the dialyzer 2 are connected to the fresh dialysate chamber 11 and the used dialysate chamber 13 of the closed type water-removal control apparatus 1 respectively through the fresh dialysate line 3 and the used dialysate line 4. Further, an inlet and an outlet of the blood flow path 22 of the dialyzer 2 are respectively connected with the artery side blood line 6 and the vein side blood line 7.

In a dialysis treatment, first, the inside of the blood circulation path including the dialyzer 2, the artery side blood line 6 and the vein side blood line 7 needs to be cleaned and primed.

Figure 4:
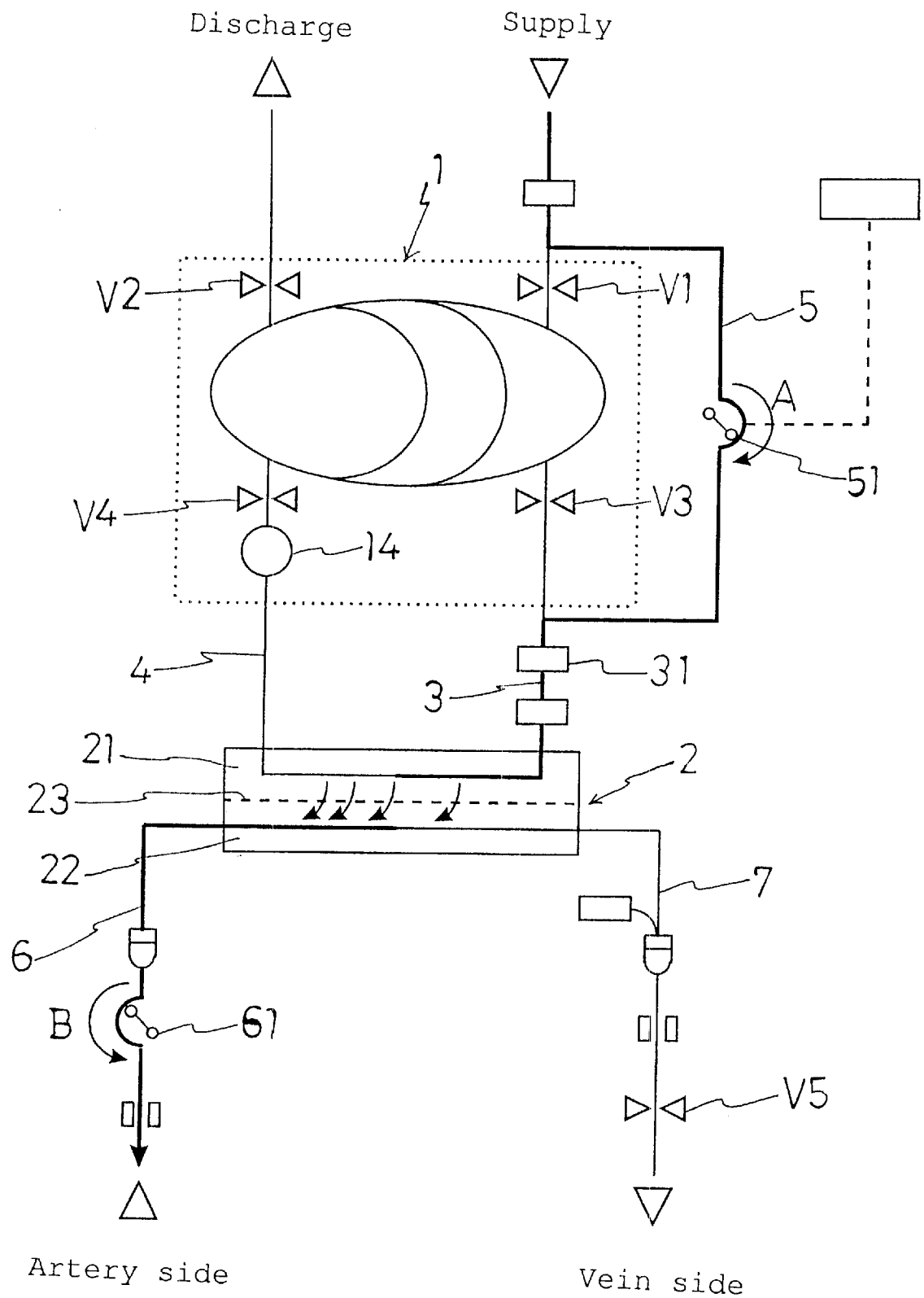
FIG. 4 is an explanatory view illustrating a cleaning and priming operation of an artery side of a blood circulation path in the system of FIG. 1.
Figure 5:
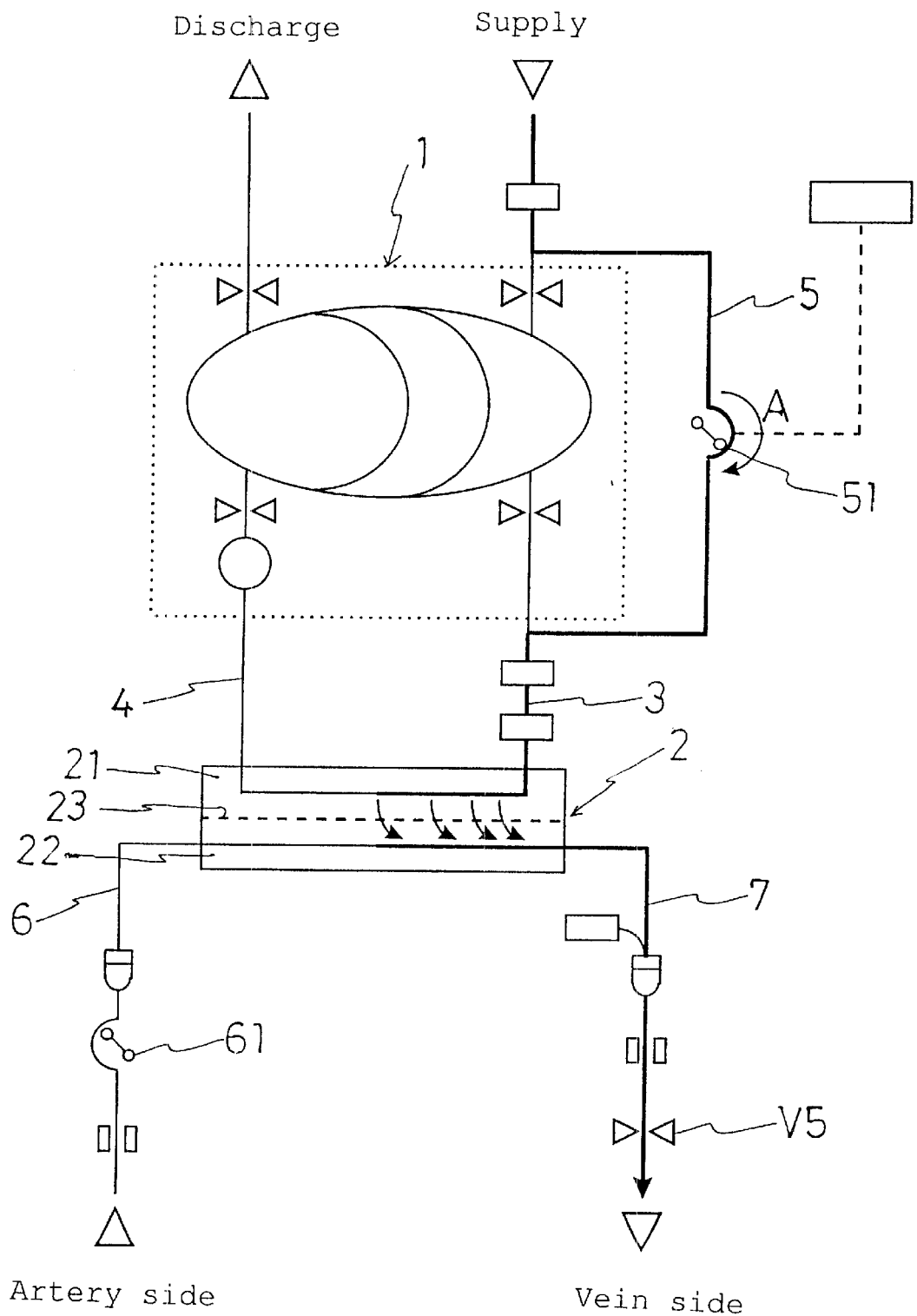
FIG. 5 is an explanatory view illustrating the cleaning and priming operation of a vein side of the blood circulation path in the system of FIG. 1.

In a state of closing the opening and closing valves V1, V2, V3, V4 and V5, as illustrated in FIG. 4, the dialysate pressurizing pump 51 and the blood pump 61 are operated in directions of arrow marks A and B. Then, a fresh dialysate from a dialysate source is supplied to the dialy sate flow path 21 of the dialyzer 2 via the dialysate pressurizing line 5 and the endotoxin filter 31 by the dialysate pressurizing pump 51, flows to the side of the blood flow path 22 by permeating the dialysis membrane 23 in the dialyzer 2 and is discharged to the outside via the artery side blood line 6. The inside of the blood circulation path on the artery side is cleaned and primed during this procedure. Next, as illustrated in FIG. 5, when the blood pump 61 is stopped and the opening and closing valve V5 is opened, the fresh dialysate supplied to the dialysate flow path 21 of the dialyzer 2 similarly flows to the side of the blood flow path 22 and is discharged to the outside via the vein side blood line 7 in this case. The inside of the blood circulation path on the vein side is cleaned and primed during this procedure. When the cleaning and priming operation in the blood circulation path is finished, the dialysate pressurizing pump 51 is stopped, the cleaning solution in the blood circulation path is substituted by a heparinized physiological saline (however, a line for supplying the physiological saline needs to be installed separately), as necessary and, thereafter, the opening and closing valve V5 is closed (refer to FIG. 6) and the blood lines 6 and 7 are connected to the vein of a patient for which the dialysis treatment has been prepared.

Figure 2:
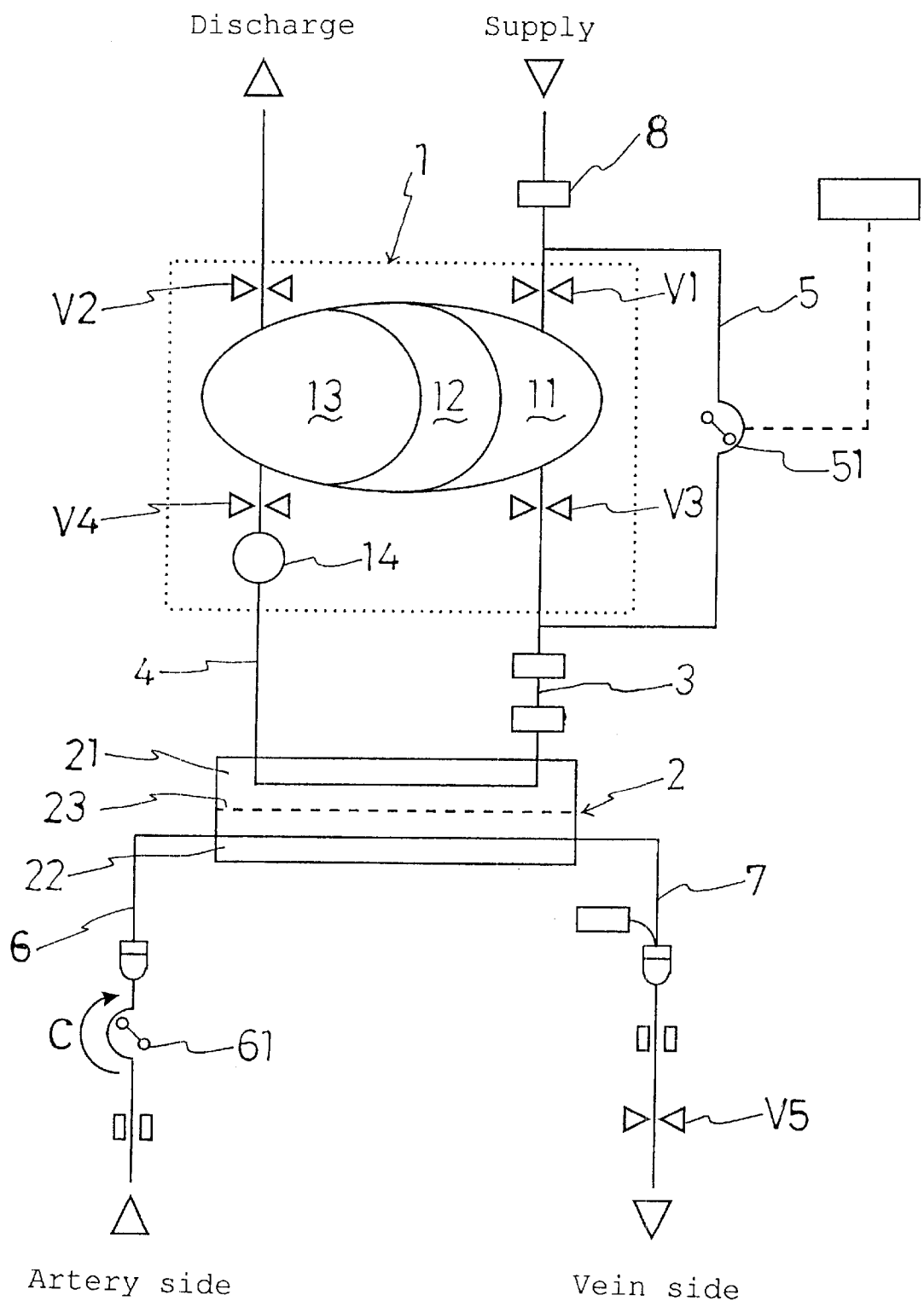
FIG. 2 is an explanatory view illustrating a state of carrying out a dialysis treatment in the system of FIG. 1.

First, when the opening and closing valves V1 and V2 are opened, the dialysate from the dialysate source fills the fresh dialysate chamber 11 of the closed-type water-removal control apparatus 1 via the endotoxin filter 8. When the fresh dialysate chamber 11 becomes full with the dialysate from the dialysate source, as illustrated in FIG. 2, the opening and closing valves V1 and V2 are closed, the opening and closing valves V3 and V4 are opened (at this point, the communication line of the dialysate becomes a closed line), a solution pressurizing pump 14 is operated, and the blood pump 61 is operated in a direction of an arrow mark C. Then, the fresh dialysate is supplied from the fresh dialysate chamber 11 to the dialysate flow path 21 of the dialyzer 2 via the fresh dialysate line 3 and the blood of the patient is delivered to the blood flow path 22 by passing though the artery side blood line 6 by the blood pump 61. The blood is dialyzed in the dialyzer through the dialysis membrane 23 and is returned to the patient via the vein side blood line 7. Meanwhile, the used dialysate fills the used dialysate chamber 13 via the used dialysate line 4. In this case, the communication line of the dialysate becomes the closed line and, therefore, water can accurately be removed by discharging the silicone oil of the partition wall 12 from the chamber. When the used dialysate chamber 13 becomes full with the used dialysate, the opening and closing valves V1 and V2 are opened and the opening and closing valves V3 and V4 are closed. Then, the dialysate from the dialysate source fills the fresh dialysate chamber 11 via the endotoxin filter 8 and the used dialysate having a volume equal to that of the fresh dialysate supplied to the fresh dialysate chamber 11, is discharged from the used dialysate chamber 13. Thereafter, a similar dialysis operation is repeated.

There is a case in which the solution needs to be replenished when the blood pressure of the patient is lowered in the dialysis treatment.

Figure 3:
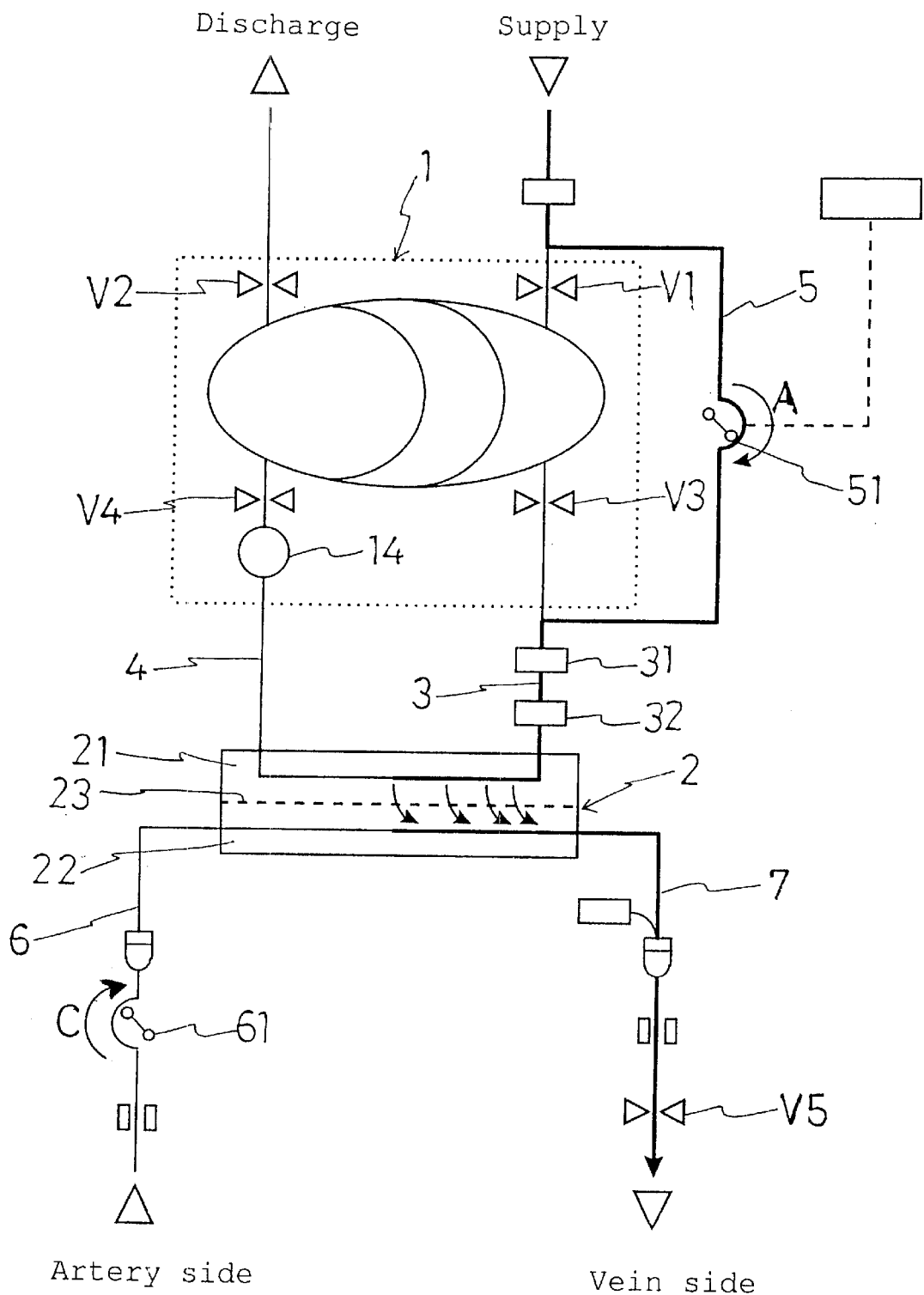
FIG. 3 is an explanatory view illustrating a solution replenishing operation under a dialysis treatment in the system of FIG. 1.

In that case, as illustrated in FIG. 3, the dialysate pressurizing pump 51 of the dialysate pressurizing line 5 is operated in the direction of the arrow mark A. The dialysate pressurizing line 5 is connected to the fresh dialysate line 3 or the used dialysate line 4 (not shown) and the fresh dialysate line 3 is preferably installed with the endotoxin filter 31. The fresh dialysate from the dialysate source is delivered to the fresh dialysate line 3 via the dialysate pressurizing line 5 by the dialysate pressurizing pump 51 and is supplied to the dialysate flow path 21 of the dialyzer 2 via the endotoxin filter 31 and the solution pressure sensor 32. Then, since the communication line of the dialysate becomes a closed line, the fresh dialysate exceeding the volume of the constant volume chamber permeates the dialysis membrane 23 of the dialyzer 2 and flows from the dialysate flow path 21 to the blood flow path 22, and is supplied into the body of the patient via the vein side blood line 7.

When the dialysis treatment is finished, blood remaining in the blood circulation path needs to be returned into the body (vein) of the patient (referred to as recovery of blood).

Figure 6:
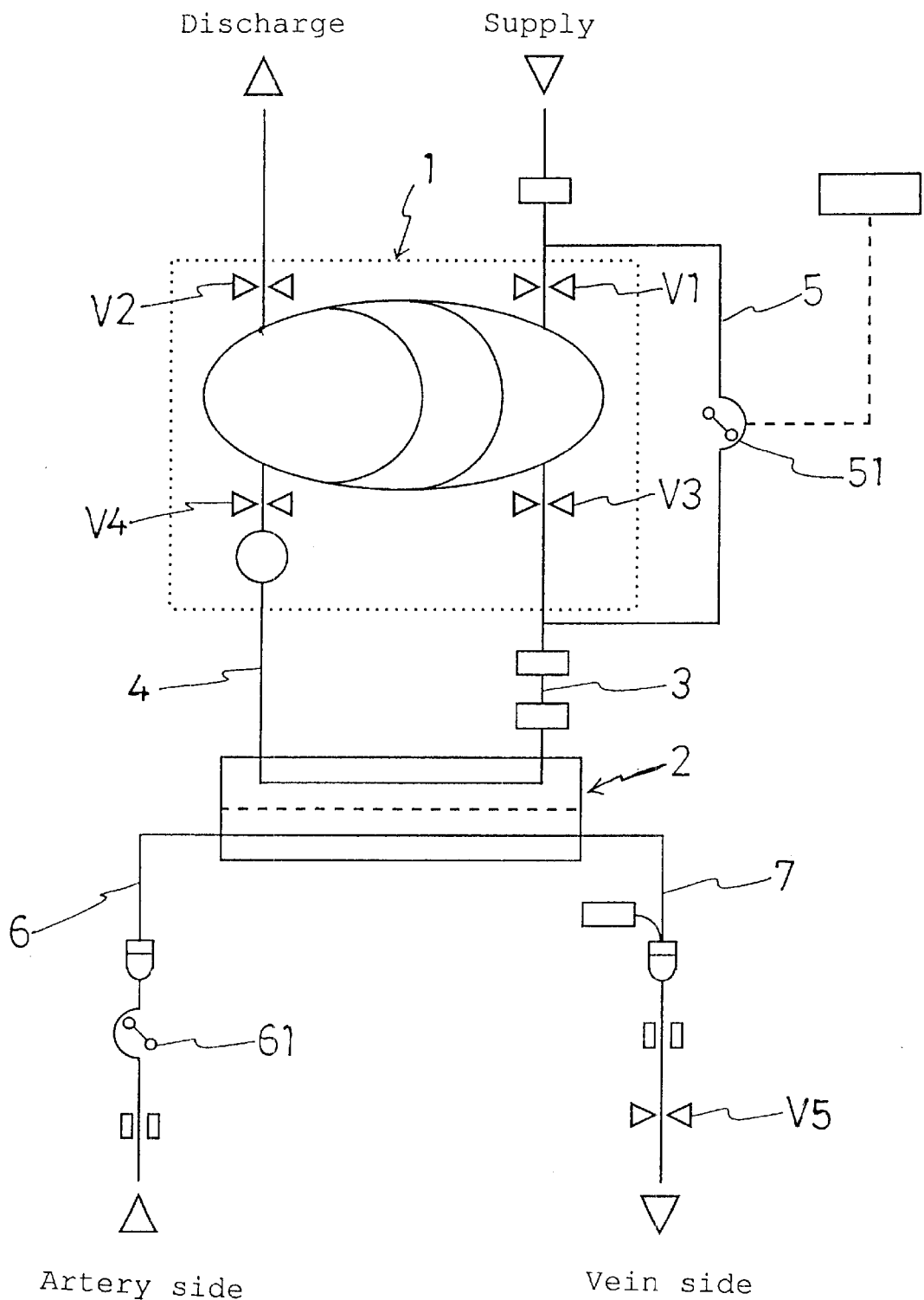
FIG. 6 is an explanatory view illustrating a state of finishing the cleaning and priming operation in the system of FIG. 1.
Figure 7:
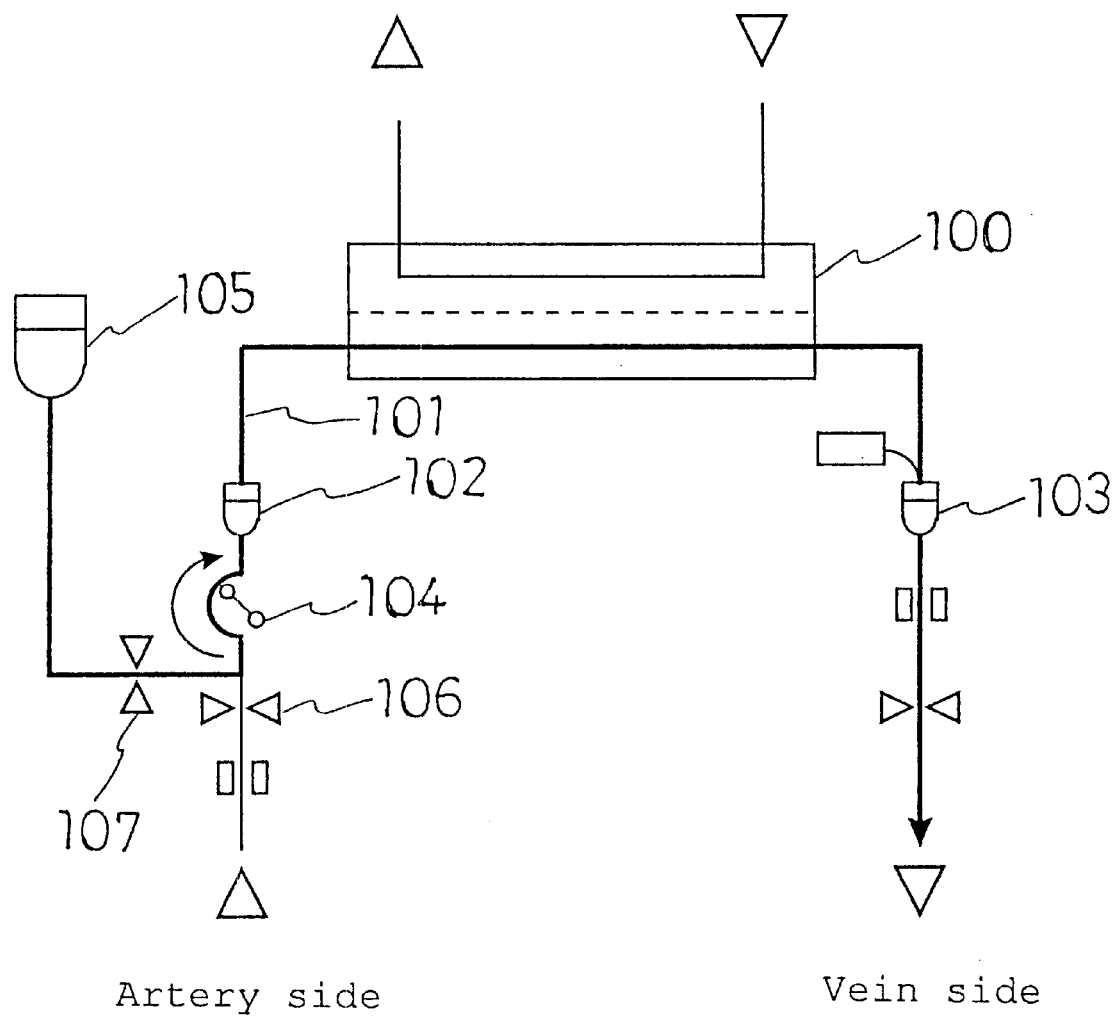
FIG. 7 is an explanatory view of a conventional solution replenishing method.
Figure 8:
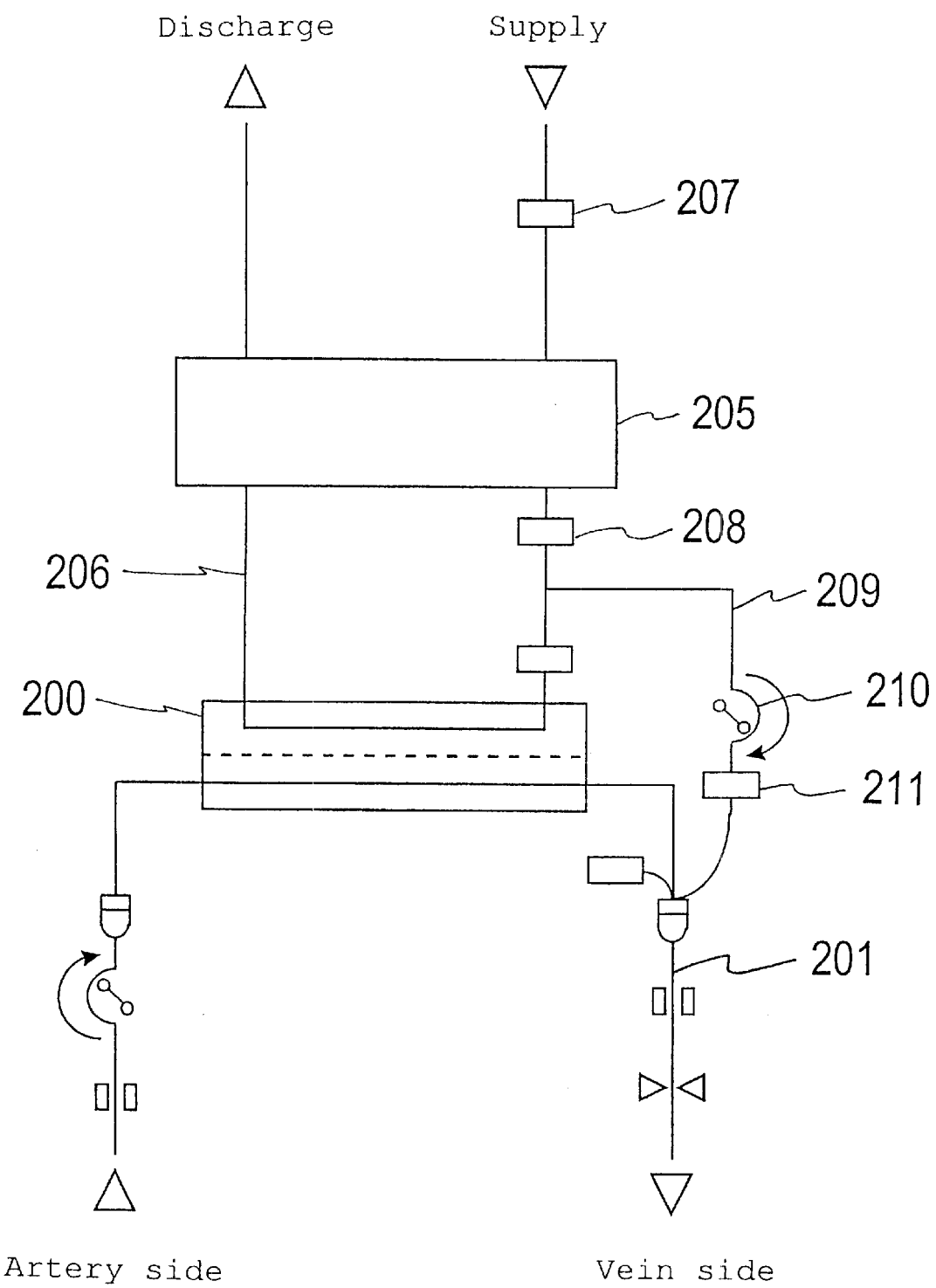
FIG. 8 is an explanatory view of another conventional solution replenishing method.

The recovery of the blood can be carried out by a method quite similar to the method of cleaning and priming. That is, the opening and closing valves V3, V4 and V5 are closed, as illustrated in FIG. 4, the dialysate pressurizing pump 51 and the blood pump 61 are operated in the directions of the arrow marks A and B, then, the fresh dialysate flows into the blood circulation path at the artery side and the blood in the artery side blood circulation path is returned into the body of the patient. Next, as illustrated in FIG. 5, the blood pump 61 is stopped and the opening and closing valve V5 is opened. Then, in this case, the fresh dialysate flows into the blood circulation path on the vein side and blood in the vein side blood circulation path is returned into the body of the patient. When the recovery operation of blood in the blood circulation path has been finished, as illustrated in FIG. 6, the dialysate pressurizing pump 51 is stopped, the opening and closing valve V5 is closed and the blood lines 6 and 7 are detached from the vein of the patient.

Further, the dialysate pressurizing pump 51 can be controlled by dialysate line pressure detected by the solution pressure sensor 32 (in the drawing, fresh dialysate pressure is detected) or can be controlled by blood line pressure detected by the line pressure sensor 71 (in the drawing, vein pressure is detected) or can be controlled by both the dialysate line pressure and the blood line pressure as necessary. Further, it is preferable that the dialysate pressurizing pump 51 is set with a flow speed or a dialysate pressurizing amount. Further, air bubble sensor 63 can be installed in the artery side blood line 6 to confirm finishing of the artery side cleaning and priming.

As is apparent from the above description, according to the invention, fresh dialysate from a dialysate source can be used as a replenisher solution, as a solution for blood recovery and as a cleaning and priming solution and accordingly, there is no need of conducting a troublesome setup operation which is conventionally carried out in replenishing the solution, cleaning and priming the blood line and recovering blood and labor of persons engaged in medical treatment can be considerably reduced. Further, the flow rate of the replenishing solution can be set easily and accurately. Further, the use of sterilized physiological saline in recovering blood is dispensed with and, therefore, the cost of dialysis treatment can be significantly reduced.

What is claimed is:

1. A method of cleaning and priming a dialysis system where the dialysis system comprises
 a dialyzer having a dialysate flow path and a blood flow path partitioned by a dialysis membrane;
 a closed-type water-removal control apparatus for controlling a difference between volumes of a fresh dialysate flowing into the dialyzer and a used dialysate flowing out of the dialyzer by removing a volume of water, said closed-type water-removal control apparatus including a fresh dialysate chamber and a used dialysate chamber;

a fresh dialysate supply line extending from a source of fresh dialysate to the fresh dialysate chamber;

a dialysate line connecting the closed-type water-removal control apparatus and the dialysate flow path of the dialyzer, said dialysate line including an inlet line to the dialyzer connected to the fresh dialysate chamber and an outlet line from the dialyzer connected to the used dialysate chamber;

a dialysate pressurizing line connected to said fresh dialysate supply line at a junction with said fresh dialysate supply line and connected to said inlet line to the dialyzer at a junction with said inlet line to the dialyzer;

a dialysate pressurizing pump provided in the dialysate pressurizing line between said junctions;

an artery side blood line connected to a blood inlet of the dialyzer;

a blood pump provided in the artery side blood line; and a vein side blood line connected to a blood outlet of the dialyzer;

said method comprising pressuring the dialysate from the fresh dialysate source into said dialysate line via said dialysate pressurizing line to cause the dialysate to flow through the dialysis membrane of the dialyzer into the blood flow path.

2. The cleaning and priming method of a dialysis system according to claim 1:

wherein the dialysis system is a dialysis system for a central dealysate supply.

* * * * *

UNITED STATES PATENT AND TRADEMARK OFFICE
CERTIFICATE OF CORRECTION

PATENT NO.    : 6,551,513 B2
DATED         : April 22, 2003
INVENTOR(S)   : Taku Nikaido et al.

It is certified that error appears in the above-identified patent and that said Letters Patent is hereby corrected as shown below:

<u>Column 8,</u>
Line 14, "central dealysate supply" should read -- central dialysate supply --.

Signed and Sealed this

Nineteenth Day of August, 2003

JAMES E. ROGAN
*Director of the United States Patent and Trademark Office*